(12) United States Patent
Roman

(10) Patent No.: US 7,313,257 B2
(45) Date of Patent: Dec. 25, 2007

(54) HANDHELD OPTICAL DIAGNOSTIC DEVICE HAVING IMAGE SYSTEM ARRAY

(75) Inventor: Juan Felix Roman, St. Edmunds (GB)

(73) Assignee: Siemens Medical Solutions Diagnostics, Tarrytown, NY (US)

( * ) Notice: Subject to any disclaimer, the term of this patent is extended or adjusted under 35 U.S.C. 154(b) by 0 days.

(21) Appl. No.: 10/589,911

(22) PCT Filed: Mar. 3, 2005

(86) PCT No.: PCT/US2005/007227

§ 371 (c)(1),
(2), (4) Date: Aug. 18, 2006

(87) PCT Pub. No.: WO2005/088519

PCT Pub. Date: Sep. 22, 2005

(65) Prior Publication Data

US 2007/0183930 A1    Aug. 9, 2007

(51) Int. Cl.
*G06K 9/00* (2006.01)
(52) U.S. Cl. .................. 382/128; 436/165; 436/172
(58) Field of Classification Search .............. 382/128; 436/165, 172; 250/559.2
See application file for complete search history.

(56) References Cited

U.S. PATENT DOCUMENTS

| 5,279,294 | A | * | 1/1994 | Anderson et al. | ........... 600/322 |
| 5,408,535 | A | | 4/1995 | Howard, III et al. | |
| 6,184,040 | B1 | | 2/2001 | Polizzotto et al. | |
| 6,331,715 | B1 | | 12/2001 | Mauchan et al. | |
| 6,495,373 | B1 | * | 12/2002 | Mauchan | .................... 436/165 |

* cited by examiner

*Primary Examiner*—Matthew C. Bella
*Assistant Examiner*—Tom Y Lu
(74) *Attorney, Agent, or Firm*—Sampson & Associates; Noam Pollack, Siemens

(57) ABSTRACT

A self-contained, optical hand-held diagnostic device is provided with a body having a pocket-sized form factor sized and shaped for engagement by a user's hand. The body includes an integral power supply and an integral display. A channel receives reagent sample media in an indexed fit. The sample media has a plurality of spaced test areas which change color according to an amount of a constituent or property in the sample. Imagers are located within the body so that each of the imagers is superposed with one of the test areas when the sample media is indexed within the channel, to capture an image thereof. A processor is coupled with the imagers to analyze the captured images. The processor also derives a diagnosis value from the analysis, and generates an output corresponding thereto. The display is configured to receive and display the output.

38 Claims, 12 Drawing Sheets

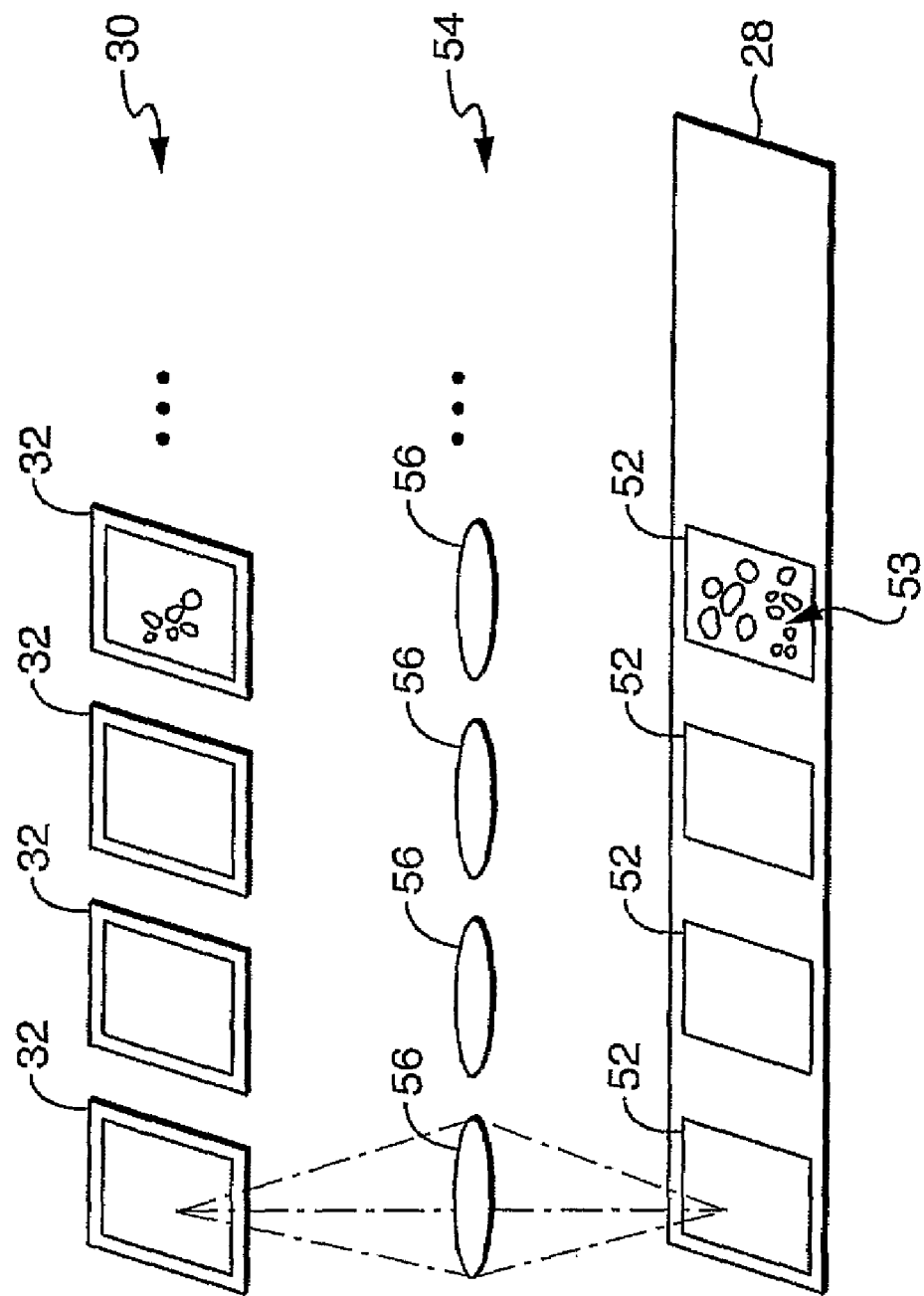

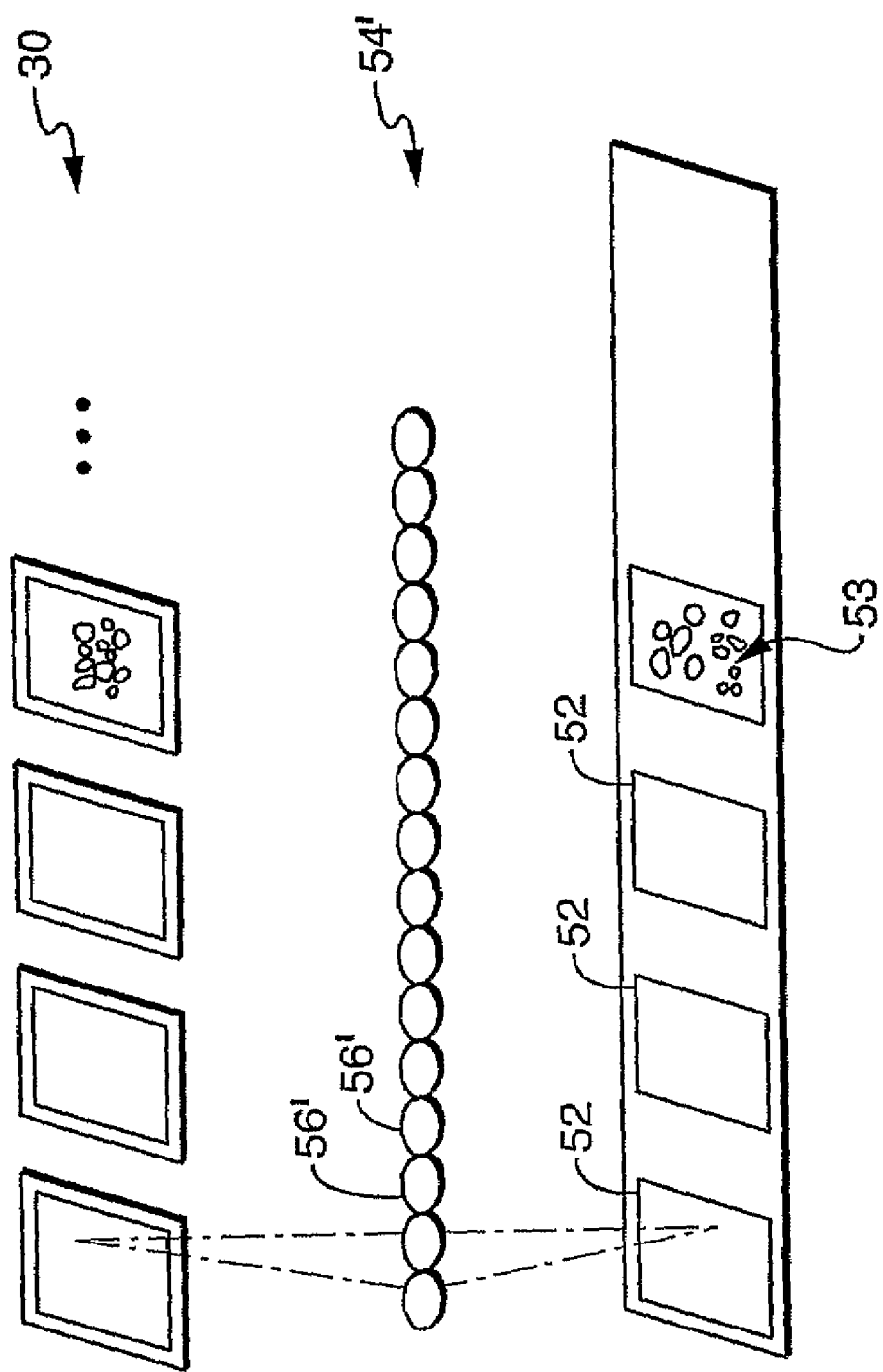

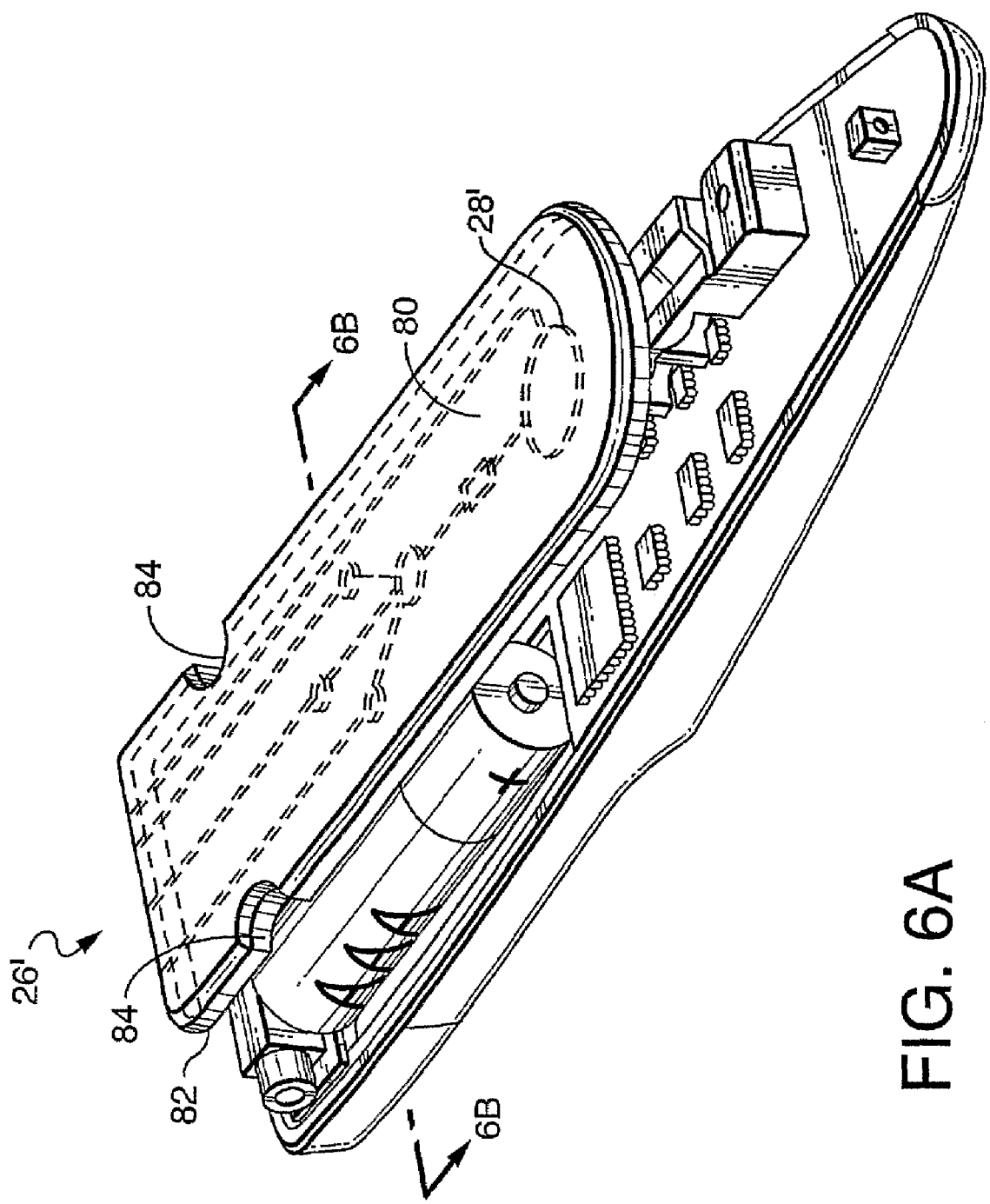

HANDHELD OPTICAL DIAGNOSTIC DEVICE HAVING IMAGE SYSTEM ARRAY

BACKGROUND

1. Technical Field

The present invention generally relates to the field of clinical chemistry. More particularly, the present invention relates to a diagnostic imaging system that analyzes the color change associated with one or more test areas on sample media following contact thereof with a liquid specimen, such as urine or blood.

2. Background Information

Throughout this application, various patents are referred to by an identifying citation. The disclosures of the patents referenced in this application are hereby incorporated by reference into the present disclosure.

Reagent test strips are widely used in the field of clinical chemistry. A test strip usually has one or more test areas, and each test area is capable of undergoing a color change in response to contact with a liquid specimen. The liquid specimen usually contains one or more constituents or properties of interest. The presence and concentrations of these constituents or properties are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments exist that employ reflectance photometry for reading test strip color changes. These instruments accurately determine the color change of a test strip within a particular wavelength range or bandwidth. Some instruments may also measure color inconsistencies outside this bandwidth. For example, instruments such as those sold under the CLINITEK® trademark by Bayer Healthcare Diagnostics Division of Bayer HealthCare LLC (Medfield, Massachusetts) and/or as disclosed in U.S. Pat. No. 5,408,535, may detect features such as traces of blood within a urine specimen on a MULTISTIX® (Bayer) reagent strip. After the urine specimen contacts the test pad of a MULTISTIX® reagent strip, intact blood cells appear as small green blotches on the yellow test area. These existing strip readers can detect both the overall color of the test pad and the small blotches of green.

U.S. Pat. No. 5,055,261 discloses a multiple-strip reading instrument utilizing reflectance photometry to read test strips. An operator sequentially places the test strips transversely in a loading area. An arm orients the test strips on rails extending from the loading area to one or more reading stations employing read heads.

This instrument includes an indexing mechanism that incrementally advances the strips in spaced parallel relation a predetermined distance along the rails. After each incremental advance, each test strip dwells for a predetermined time period in its new position. Consequently, individual test strips sequentially advance to a reading position where, during the dwell period, certain test areas are read. Subsequently, the instrument advances the test strip to the next reading position where the instrument reads the other test areas on the test strip with longer incubation times.

An instrument embodied in U.S. Pat. No. 5,143,694 also transports test strips from a strip loading area, along a transport path under the read heads, and then to a waste receptacle.

A common feature of these instruments is that their relative size and complexity, particularly with respect to those utilizing automated test pad transport systems, render them relatively unportable. Rather, these devices tend to be installed at a dedicated testing center or laboratory, where samples are aggregated and tested in bulk. Unfortunately, such aggregation of samples from multiple patients presents opportunities for error due to mislabeling of the samples and/or the test results. Moreover, in many instances, the time required for transporting the samples to and from the processing center, and for testing and recording the results, may be problematic.

A need therefore exists for an improved diagnostic testing device that enables a care provider to obtain quick and accurate test results without the need for sending sample media to a remote testing center for processing.

SUMMARY

An aspect of the invention includes a self-contained, optical hand-held diagnostic device having a body of pocket-sized form factor sized and shaped for engagement by a user's hand. The body includes an integral power supply and an integral display. A channel receives reagent sample media in an indexed fit therein. The sample media has a plurality of spaced test areas which change color according to an amount of a constituent or property in the sample. Imagers are located within the body so that each of the imagers is superposed with one of the test areas when the sample media is indexed within the channel, to capture an image thereof. A processor is coupled with the imagers to analyze the captured images. The processor also derives a diagnosis value from the analysis, and generates an output corresponding thereto. The display is configured to receive and display the output.

Another aspect of the invention includes a self-contained, optical hand-held diagnostic device. The device includes a body having a pocket-sized form factor sized and shaped for engagement by a user's hand. A power supply and a display are both located integrally within the body. A channel is configured for receiving a reagent test strip therein, the test strip having a plurality of test pads disposed in spaced relation thereon, each of the test pads configured to react with a sample and to change color according to an amount of a constituent or property in the sample. The channel is sized and shaped for forming an indexed fit with the test strip, and a micro-array of imagers are located within said body in fixed superposition with the channel. Each of the imagers are superposed with a respective one of the test pads when the test strip is indexed within the channel. A light source is configured to illuminate said test strip, and the imagers are configured to each capture an image of the test pad respectively superposed therewith. A processor is coupled to the imagers, and configured to analyze the captured images. The processor is also configured to derive the amount of the constituent or property in the sample, and to generate an output signal corresponding thereto. The display is configured to receive the output signal and display the amount of constituent or property.

A further aspect of the invention includes a method for reading reagent sample media, the sample media having test areas spaced thereon, each of the test areas being configured to react with a sample and to change color according to an amount of a constituent or property in the sample. The method includes receiving the sample media into a holder of a unitary, self-contained, optical hand-held diagnostic device having an integral power supply and display, in which the holder defines a channel sized and shaped for forming an indexed fit with the sample media. The method further includes capturing images of the test areas with a micro-array of imagers located within the body, in which each imager is superposed with one of the indexed test areas. The images of the test areas are analyzed with an integral processor, to derive the amount of the constituent or property in the sample. An output signal corresponding to the amount is then generated and transmitted to the integral display.

BRIEF DESCRIPTION OF THE DRAWINGS

The above and other features and advantages of this invention will be more readily apparent from a reading of the following detailed description of various aspects of the invention taken in conjunction with the accompanying drawings, in which:

FIG. 3 is a schematic view of operative portions useful in various embodiments of the present invention;

FIG. 4 is a view similar to that of FIG. 3, of alternative operative portions useful in various embodiments of the present invention;

FIG. 6A is a view similar to that of FIG. 5A, of an alternate embodiment of the present invention;

DETAILED DESCRIPTION

Figure 1:
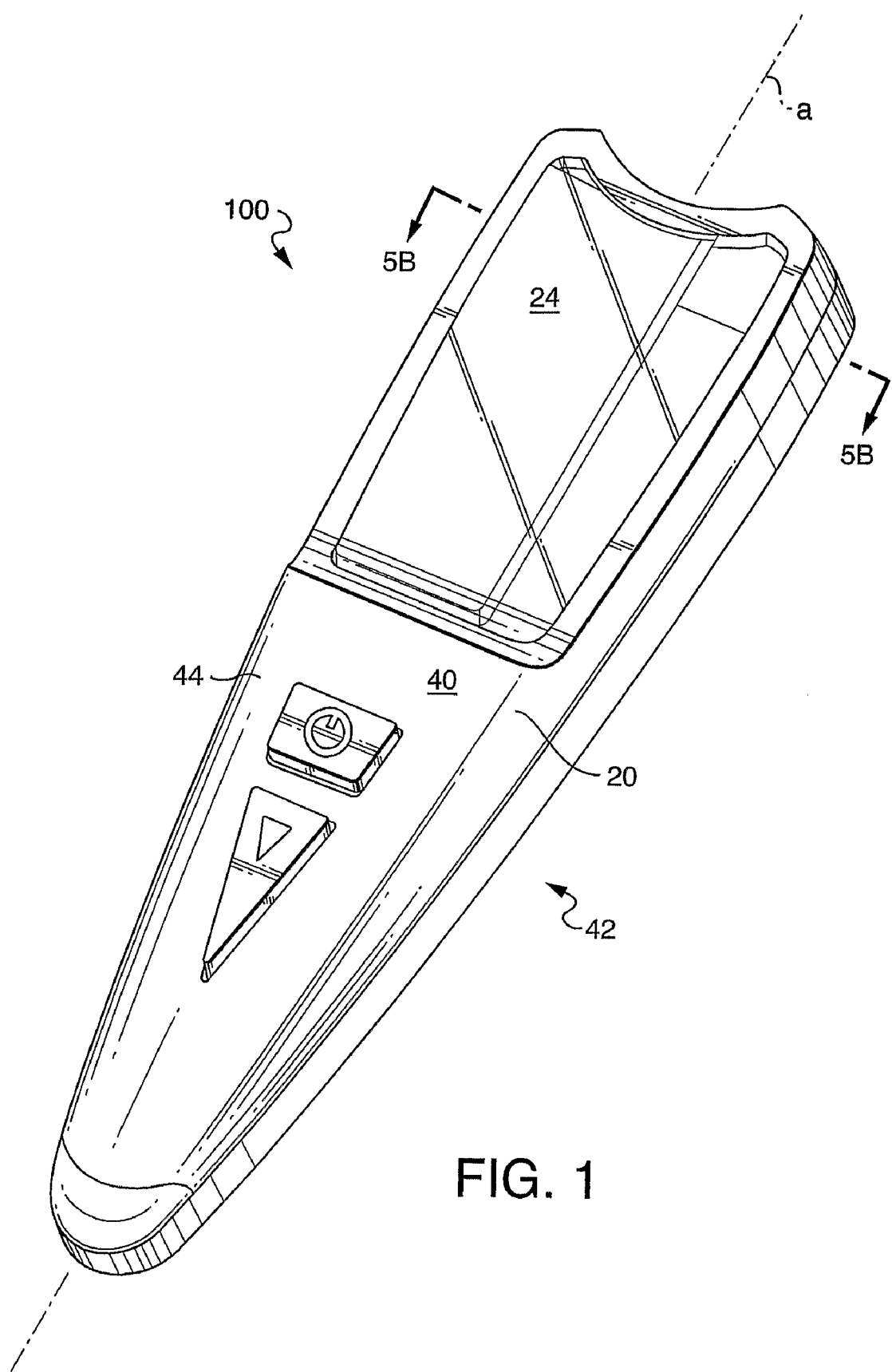
FIG. 1 is a perspective top view of an embodiment of the present invention.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Figure 2:
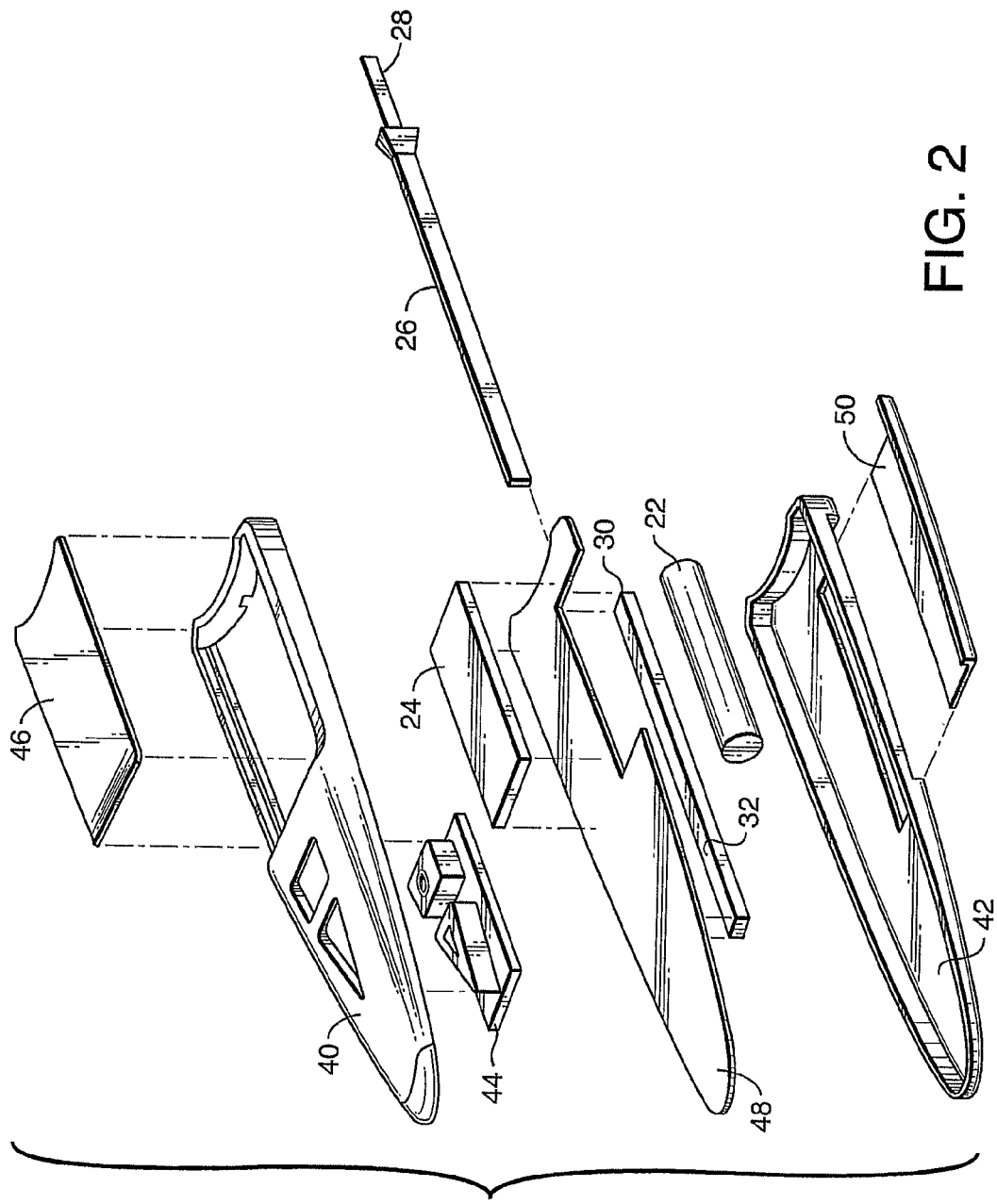
FIG. 2 is a perspective, exploded view of the embodiment of FIG. 1.

An overview of an embodiment of the invention is provided with reference to FIGS. 1 & 2. This embodiment includes a handheld optical diagnostic device 100 for analyzing reagent sample media. Device 100 is a self-contained, solid-state tool of pocket-size form factor sized and shaped for convenient engagement by a user's hand. This device includes a power supply (e.g., battery) 22 and integral display 24. A holder 26 forms a channel that extends axially through the body for receiving sample media 28 in a sliding, indexed fit.

As is familiar to those skilled in the art, sample media 28 may include typical urine analysis strips, having paper pads disposed in spaced relation thereon, which are soaked in chemical reagents that react with a specimen sample to change color according to the medical condition of the patient, i.e., according to an amount of constituent or property in the sample. Examples of such media 28 include the aforementioned MULTISTIX® test strips. Alternatively, sample media 28 may include a conventional immuno-assay cassette, e.g., the CLINITEST® hCG cassette (Bayer), having an area soaked in chemical reagents that react to the sample to reveal a colored line or pattern of lines according to the medical condition of the patient.

Other suitable sample media may include conventional microfluidic devices, which typically include a substrate having a series of narrow channels, e.g. on the order of microns in width, through which a fluid such as blood or urine may travel. The channels conduct the fluid to various test areas on the device. These devices enable various tests to be performed using only a small amount of fluid, e.g., using only a small drop of liquid. Examplary microfluidic devices are described in U.S. patent application Ser. No. 10/082,415 filed on Feb. 26, 2002 and entitled Method And Apparatus For Precise Transfer And Manipulation of Fluids by Centrifugal and or Capillary Forces.

For convenience and clarity, various embodiments of the present invention are described as using sample media 28 in the form of MULTISTIX® test strips, with the understanding that substantially any form of sample media may be used without departing from the spirit and scope of the present invention.

Device 100 also includes an integral micro-array 30 of imagers 32 (FIG. 5B), which will be discussed in greater detail below. Array 30 is located within body 20 in fixed superposition with holder 26, so that each imager 32 is superposed with a respective test pad 52 of test strip 28 once the strip is properly indexed within the holder.

Each imager 32 is thus positioned to conveniently capture an image of a single test pad. A main processor 34, which may include a dedicated image processor 36, analyzes the captured images, derives the amount of a constituent or property in the sample, and generates a corresponding output which appears on integral display 24.

Diagnostic device 100 thus advantageously provides a unitary, self-contained, solid-state device, that may be conveniently carried by a care provider in a pocket. For example, a physician may carry device 100 in the pocket of a lab coat while making rounds at a hospital. The device thus enables the care provider to obtain nearly instantaneous results from a wide range of tests.

This portability, and the immediacy of the test results generated thereby, advantageously enable care providers to collect, test, and obtain test results during a single patient visit. This ability tends not only to improve the efficiency of the testing process, but also to reduce the potential for errors that may otherwise occur when specimens from multiple patients are sent to a centralized lab for processing. This immediate testing also tends to improve patient care by enabling relatively quick diagnoses. Embodiments of the present invention therefore tend to improve patient care and efficiency, while reducing the risk of errors.

Where used in this disclosure, the term "axial" refers to a direction relative to an element, which is substantially parallel to longitudinal axis a (FIG. 1) when the element is installed on a diagnostic device 100, 100' of the present invention. Similarly, the term "transverse" refers to a direction substantially orthogonal to the axial direction. The term "transverse cross-section" refers to a cross-section taken along a plane oriented substantially orthogonally to the axial direction.

Software associated with the various embodiments of the present invention can be written in any suitable language, such as C++; Visual Basic; Java; VBScript; Jscript; BCMAscript; DHTM1; XML and CGI. Any suitable database technology may be employed, including but not limited to versions of Microsoft Access and IMB AS 400.

Particular embodiments of the present invention will now be described in detail. With reference to FIGS. 1 & 2, body 20 of device 100 includes front and rear covers 40 & 42, respectively. Front cover 40 includes a recess sized and shaped for a keypad 44 to extend therethrough for operating the device. Cover 40 also includes a window 46 through which display 24 may be viewed. In this embodiment, keypad 44 and display 24 are both mounted on a printed circuit board (PCB) 48.

Keypad 44 may include nominally any conventional key technology, such as commonly used to operate handheld cellular telephones and the like. Alternatively, or in addition, device 100 may be provided with a voice-synthesizer to accept voice commands. Display 24 may be fabricated using any suitable technology, such as conventional Liquid Crystal Display (LCD), plasma, LED (light emitting diode), micro-display, or other display technologies. Micro-array 30 of imagers 32, and holder 26, may also be supported by PCB 48, such as on the opposite side thereof from display 24 and keypad 44. Power supply 22 is also disposed within body 20, to supply operational power to the device. In the embodiment shown, power supply 22 include a conventional battery (e.g., a 'AAA' cell). Rear cover 42 may include a battery cover 50 to facilitate battery replacement. Moreover, although a battery is shown, power supply 22 may include any currently available or subsequently developed device capable of providing the requisite operational power to device 100. Examples of such alternate power supplies include fuel cells, solar cells, and/or a connector/transformer for coupling device 100 to line voltage (e.g., 110 Volt AC) either for operating device 100, or for recharging the battery (ies).

Turning now to FIGS. 3 & 4, an embodiment of imager array 30 is described. It should be recognized that this array 30 may be incorporated into any of the diagnostic device embodiments shown and described herein. As shown, array 30 includes a series of up to N imagers 32, and is superposed with test strip 28 once strip 28 is fully inserted into holder 26 (FIG. 2). Imagers 32 may include any conventional device capable of capturing images. For example, in desired embodiments, imagers 32 include conventional CCD or CMOS devices with or without color filters fitted to them. In addition, imager array 30 may include a lens system 54, including a series of lenses 56.

In the embodiment shown, each imager 32 is operatively engaged (e.g., optically coupled) to a single lens 56. However, optionally, as shown in FIG. 4, each imager 32 may be optically coupled to multiple lenses 56', such as in the event the lens system includes a micro-lens array, denoted as 54' in FIG. 4.

The close, sliding fit of strip 28 within holder 26 advantageously provides an indexing function in which each pad 52 is automatically disposed in image-capturing alignment with one of the imagers 32 once strip 28 is fully inserted. (A sensor may be used to ascertain full insertion, as discussed below.) Such a configuration advantageously eliminates the need for a complicated system of locating multiple discrete pads 52 within the field of view of a particular imager. It also eliminates any need for an automatic feeder to move-the test strip into the field of view. Still further, although perhaps counterintuitive, the use of multiple imagers, each with a relatively small viewing area, rather than use of a single imager with a larger viewing area, advantageously enables device 100 to be relatively compact. In this regard, a relationship of at least 0.5:1, or more desirably, 1:1 correspondence of imagers 32 to pads 52 advantageously facilitates a relatively compact structure, by enabling the imagers to be placed relatively close to the test strip 28.

Figure 5A:
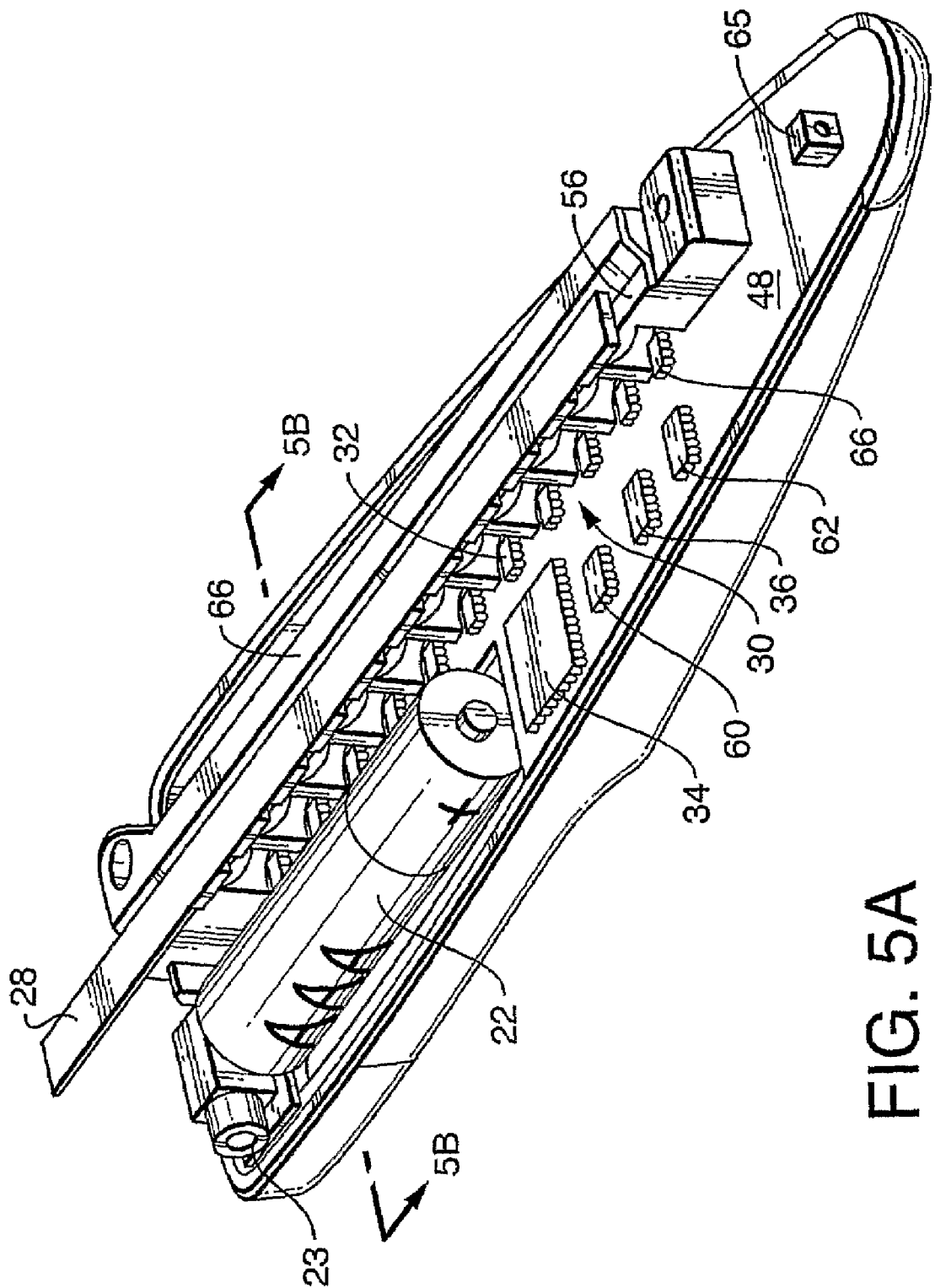
FIG. 5A is a perspective bottom view, with portions cut away for clarity, of the embodiment of FIGS. 1 & 2.
Figure 5B:
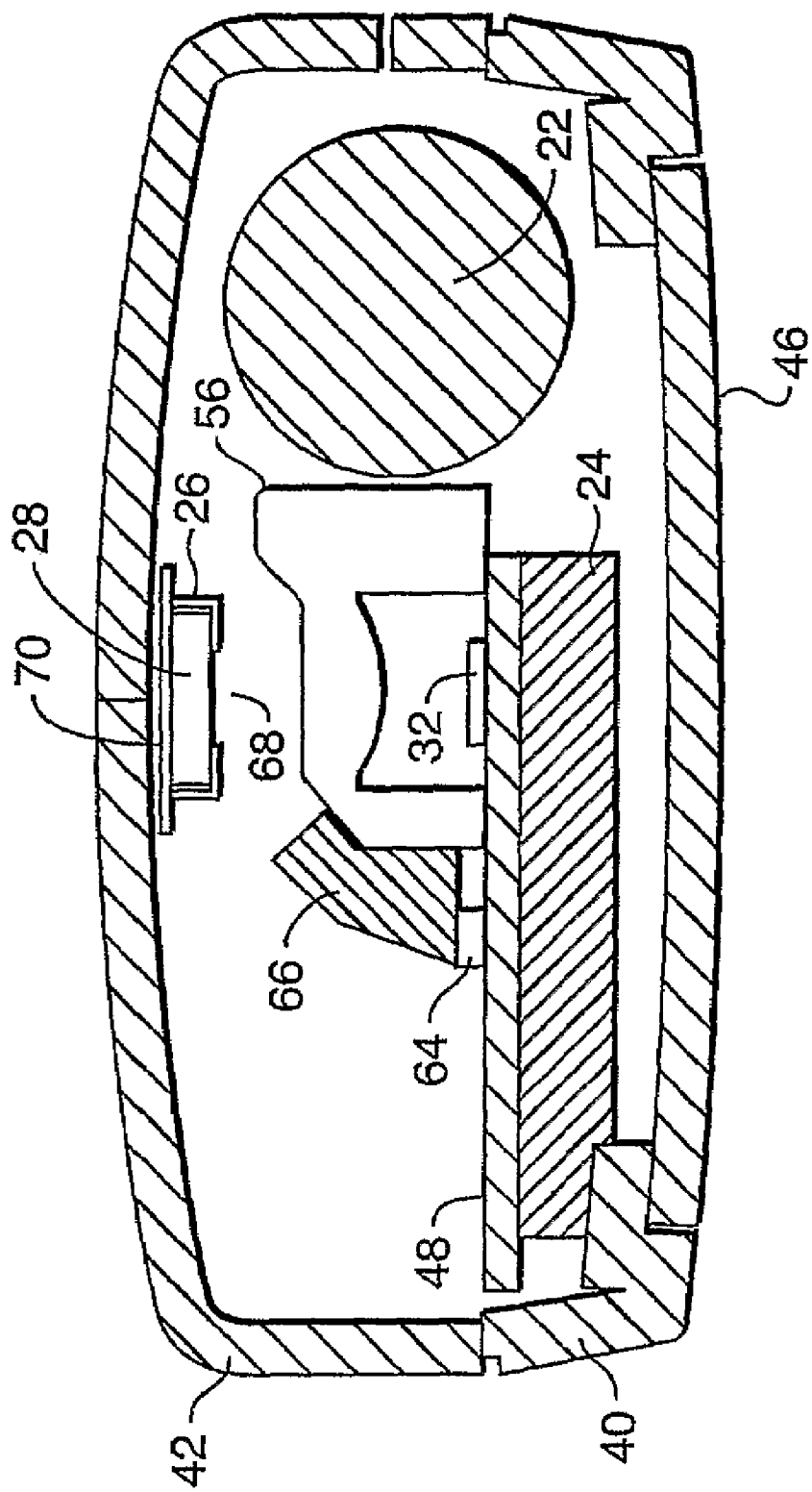
FIG. 5B is a cross-sectional view, taken along 5B-5B of FIG. 5A.

Turning now to FIGS. 5A & 5B, device 100 is shown from its underside with rear cover 42 removed (FIG. 5A) to reveal an exemplary topography of the lower side of PCB 48. As shown, main processor 34 (FIG. 5A) is mounted on PCB 48 to control the overall operation of device 100, including various other logic components such as phase-locking processor 60, image processor 36, and memory 62 (FIG. 5A). Phase-locking processor 60 may be used to prevent undesired external light effects by synchronizing light sources 64 (FIG. 5B) and imagers 32. Image processor 36 analyzes the images captured by imagers 32 to generate reflectance (color) values therefor. Processor 36 then compares these reflectance values to known values (such as may be stored in a look-up table in memory 62) corresponding to the type and amount of a particular constituent or property in the sample on the particular test pad 52, and/or an appropriate diagnosis based thereon. This reflectance analysis may be effected in the manner described in U.S. Pat. No. 5,408,535, which is fully incorporated herein by reference. As used herein, these types and amounts of a constituent or property, and/or diagnoses based thereon, are collectively referred to as 'diagnosis values'. The diagnosis values are then outputted (e.g., via main processor 34) to display 24 (FIG. 1).

Memory 62 may include any suitable device known to those skilled in the art, including RAM, ROM, and/or EPROM devices. Memory 62 is used to store an operating system for device 100, results generated by device 100, and known reference (e.g., reflectance) values, e.g., in a lookup table, for comparison to the values associated with the captured images as discussed above.

As shown in FIG. 5A, PCB 48 also supports a port 65, which may include a wireless or hard-wired connector, such as a conventional WI-FI (802.1lb) or BLUETOOTH® connection, or USB port. Port 65 facilitates the input/output of data to and from device 100. Also, in this embodiment, power supply 22 includes both a battery and a connector/transformer 23 for coupling device 100 to line voltage.

Imagers 32 of imager array 30 are mounted in axially spaced relation to one another on PCB 48. A sensor 66, which may include any suitable optical, electronic, mechanical, or electromechanical device, is located at the terminal end of the array to detect full insertion of test strip 28 (FIG. 2). Moreover, in the embodiment shown, sensor 66 is the last imager in array 30, which determines whether the strip 28 has been fully inserted simply by analyzing an image captured thereby. For example, a captured image may be examined for the presence or absence of an identifying mark or feature, such as an edge of the strip or some predetermined indicia. This last imager may then also be used for color measurement of a pad 52 in the manner described above.

As best shown in FIG. 5B, a light source 64 may be disposed on PCB 48, and may include nominally any device capable of generating sufficient light for imagers 32 to operate. Examples of suitable light sources 64 include one or more LEDs, VCSELs, or incandescent lamps (e.g. tungsten), etc.

Alternatively, particular embodiments of the present invention may simply utilize ambient light (e.g., sunlight).

A light guide 66 may be disposed to guide light from light source 64 to holder 26 for illumination of sample media (e.g., test strip) 28 inserted therein. As shown, holder 26 includes an opening or window 68 that permits an unobstructed view of media 28 by imager 32. Holder 26 may also include calibration material 70 disposed on an opposite side thereof from inserted sample media 28, so that it becomes visible to the imagers 32 when the media is removed. Calibration material 70 exhibits a known reflectance, which enables device 100 to calibrate itself between testing, as will be discussed in greater detail below.

Figure 6B:
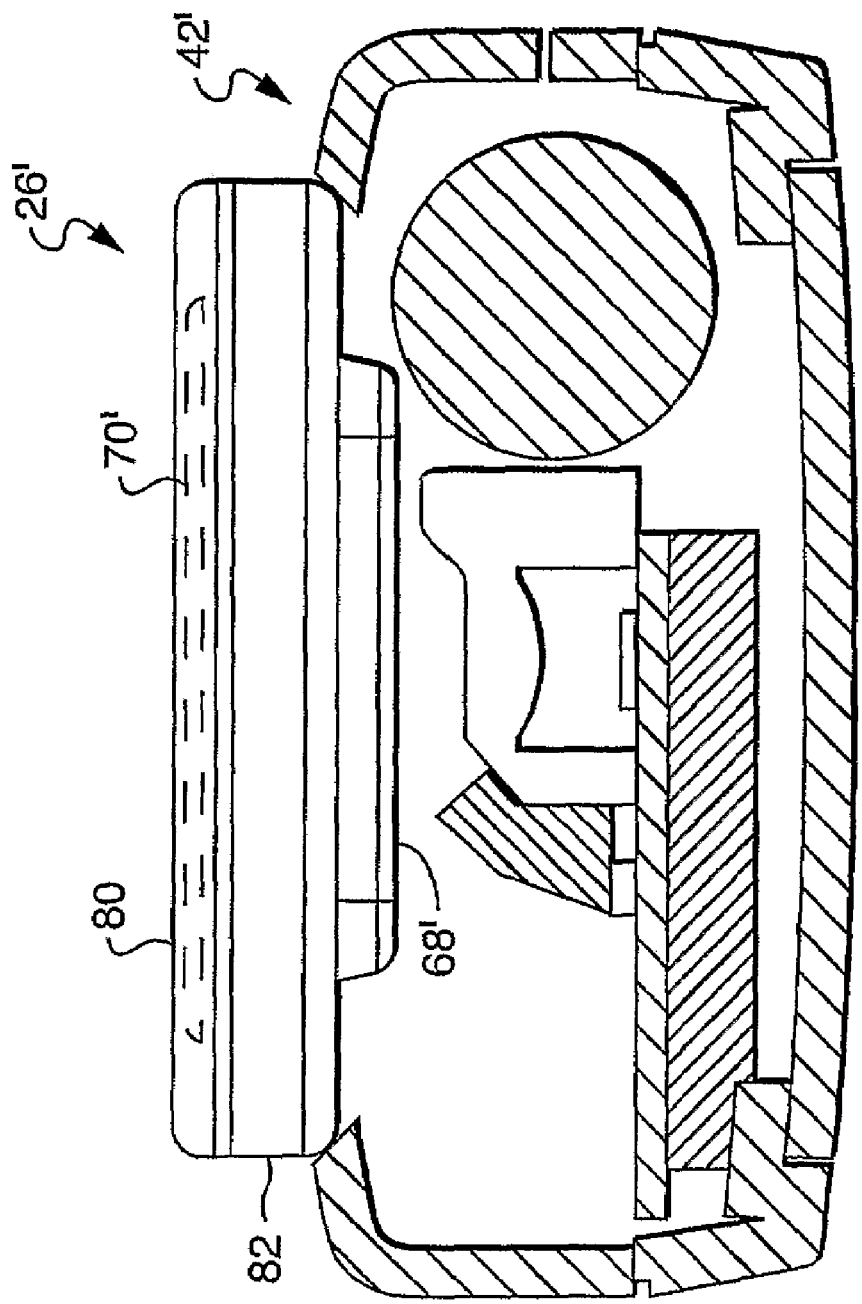
FIG. 6B is a cross-sectional view, taken along 6B-6B of FIG. 6A.

As shown in FIGS. 6A and 6B, diagnostic device 100 of FIGS. 5A and 5B may be configured for use with an alternate sample holder 26' configured to receive cassette-type media 28', such as the aforementioned immuno-cassette or microfluidic device, in an indexed manner therein. An illustrative immuno-cassette/microfluidic device 28' is shown in phantom. In the exemplary embodiment shown, holder 26' includes a cover 80, which may be removed from base 82 to permit a suitably sized and shaped media 28' to be inserted into a channel defined thereby. Features such as detents 84 may be provided to engage similar features on media 28' for proper indexing. In this particular embodiment, base 82 effectively replaces a portion of rear cover 42' and includes a window 68' that permits an unobstructed view of media 28 by imager 32. Holder 26' may also include calibration material 70' disposed on an opposite side thereof from inserted sample media 28, such as on the cover 80 as shown in phantom (FIG. 6B) so that it becomes visible to the imagers 32 when the media is removed.

The various features of holder 26' and related components are merely exemplary, and the skilled artisan should recognize that any number of approaches may be used to enable embodiments of this invention to 'read' immuno-cassettes/microfluidic media and the like, without departing from the spirit and scope of this invention.

Figure 7:
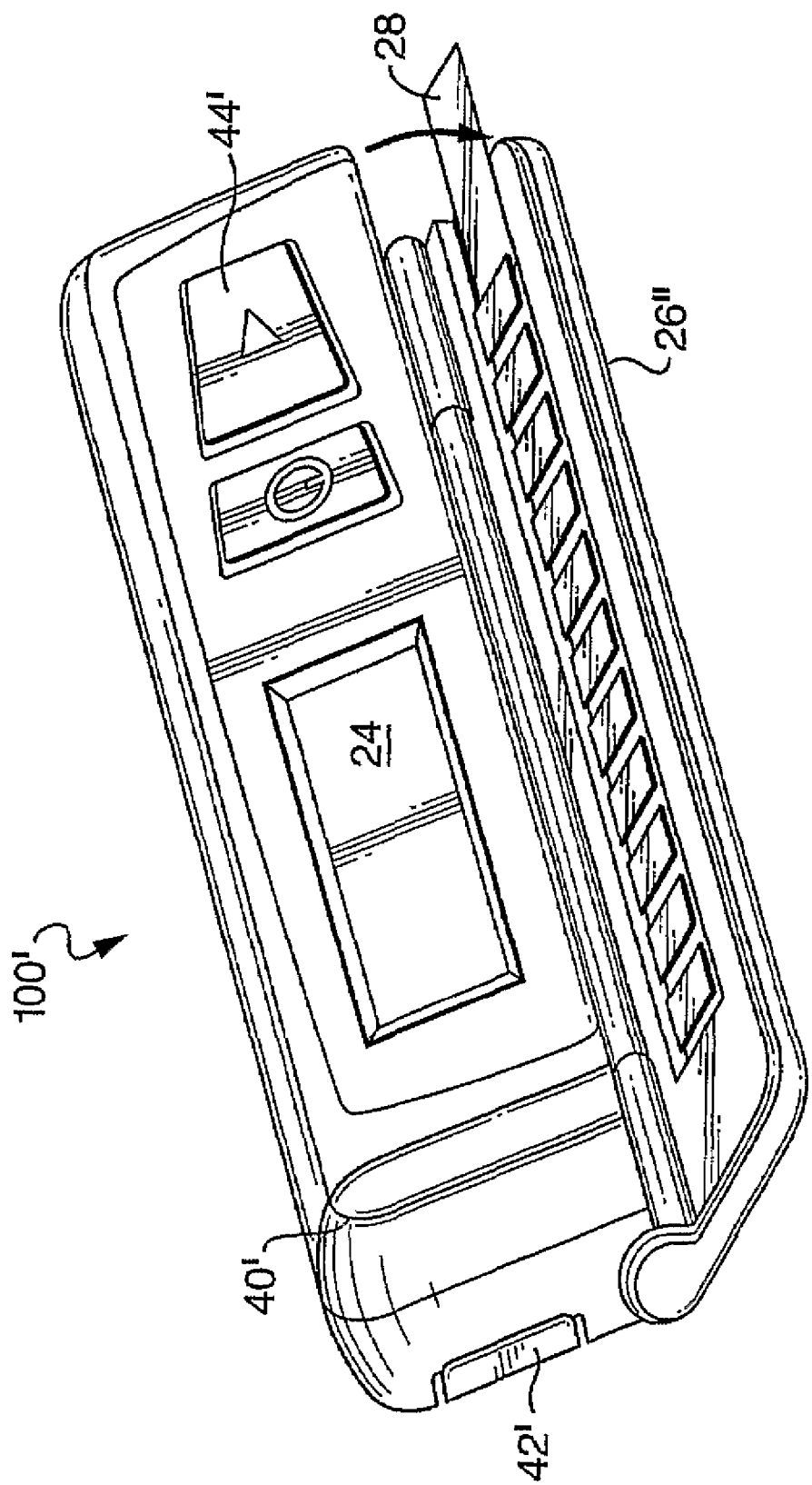
FIG. 7 is a view similar to that of FIG. 1, of an alternate embodiment of the present invention.
Figure 8:
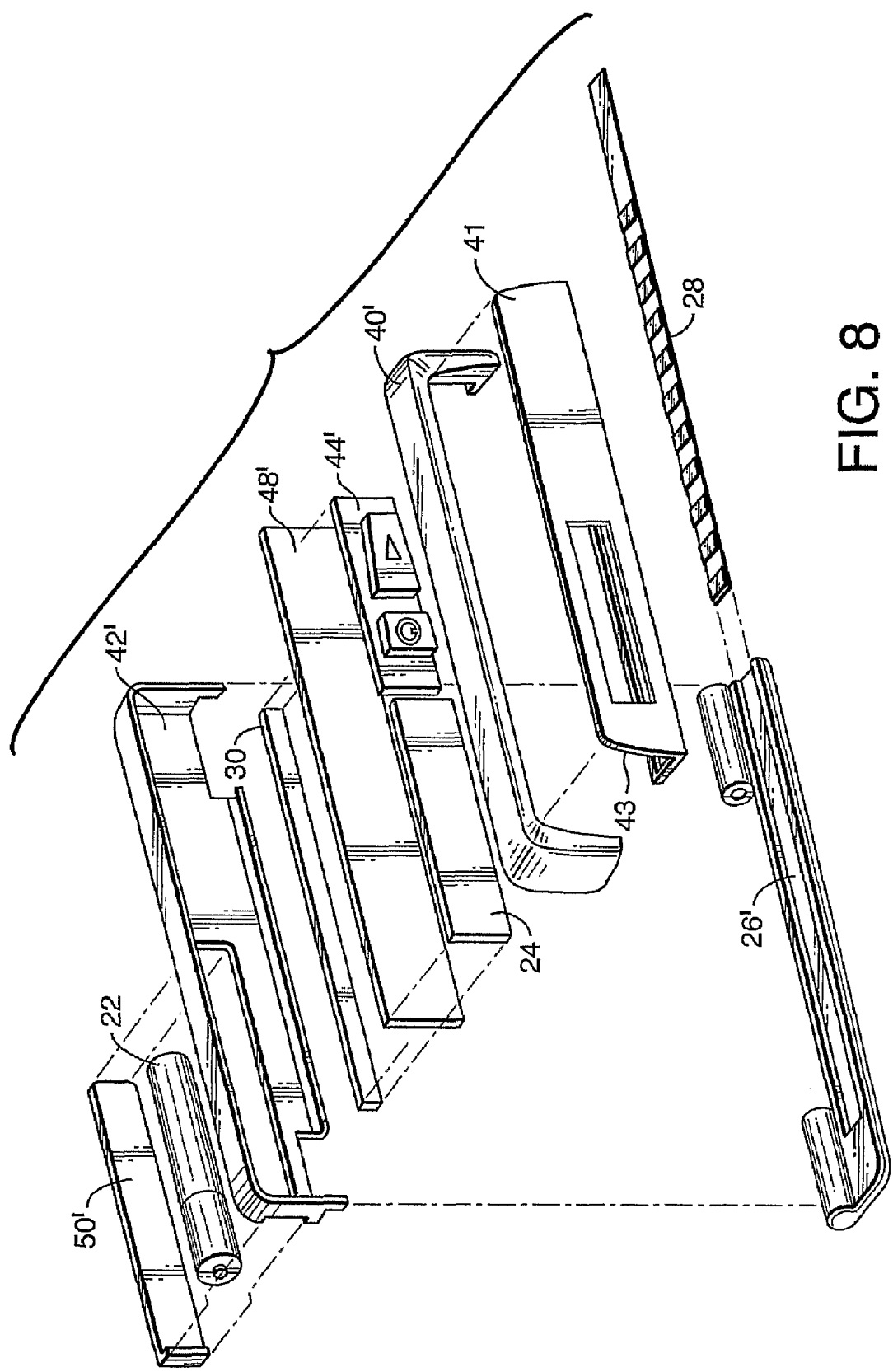
FIG. 8 is a perspective, exploded view of the embodiment of FIG. 7.

Turning now to FIGS. 7 & 8, an alternate embodiment of the present invention is shown as diagnostic device 100". This device 100' is substantially similar to device 100, with various distinctions which will now be discussed. As shown, this embodiment includes a rear cover 42' with a power supply 22 and door 50', an array 30 of imagers, a PCB 48', and keypad 44, display 24 and a front cover 40', all of which function similarly to similar or identical components of device 100 discussed above. In this particular embodiment, front cover 40' includes a front bezel 41 fabricated as a discrete component, and which has a generally L-shaped transverse cross-section (best shown in FIG. 8). Bezel 41 thus effectively forms a top surface, through which the keypad 44 extends (and through which display 24 is viewable), and a side surface having a window or recess 43 disposed therein. Although shown as two discrete components, cover 40' and bezel 41 may be constructed in any number of components, including a single, integrated component, or an assembly with several discrete components.

A distinction of this device 100' relative to device 100, is the use of movable, hinged, holder 26". As shown, holder 26" is fabricated in the form of a planar tray having a recess that defines a channel sized and shaped for slidably receiving test strip 28 therein. Referring to FIG. 7 in particular, holder 26" is hingedly movable between an open position as shown, and a closed position shown in phantom. In this embodiment, when in the open position, the plane of holder 26" extends obliquely relative to bezel 41, to enable a user to conveniently place test strip 28 therein as shown. The user may then rotate holder 26" to its closed position, in which the plane of holder 26" (and test strip 28), is substantially parallel to the side surface and to window 43. In this closed position, test strip 28 is properly indexed, and visible to imager array 30 through window 43. The skilled artisan will thus recognize that imager array 30 is configured to capture images in a viewing direction which is substantially parallel to the plane of PCB 48'. However, embodiments of this invention may include imager arrays 30 disposed for nominally any viewing direction.

Figure 9:
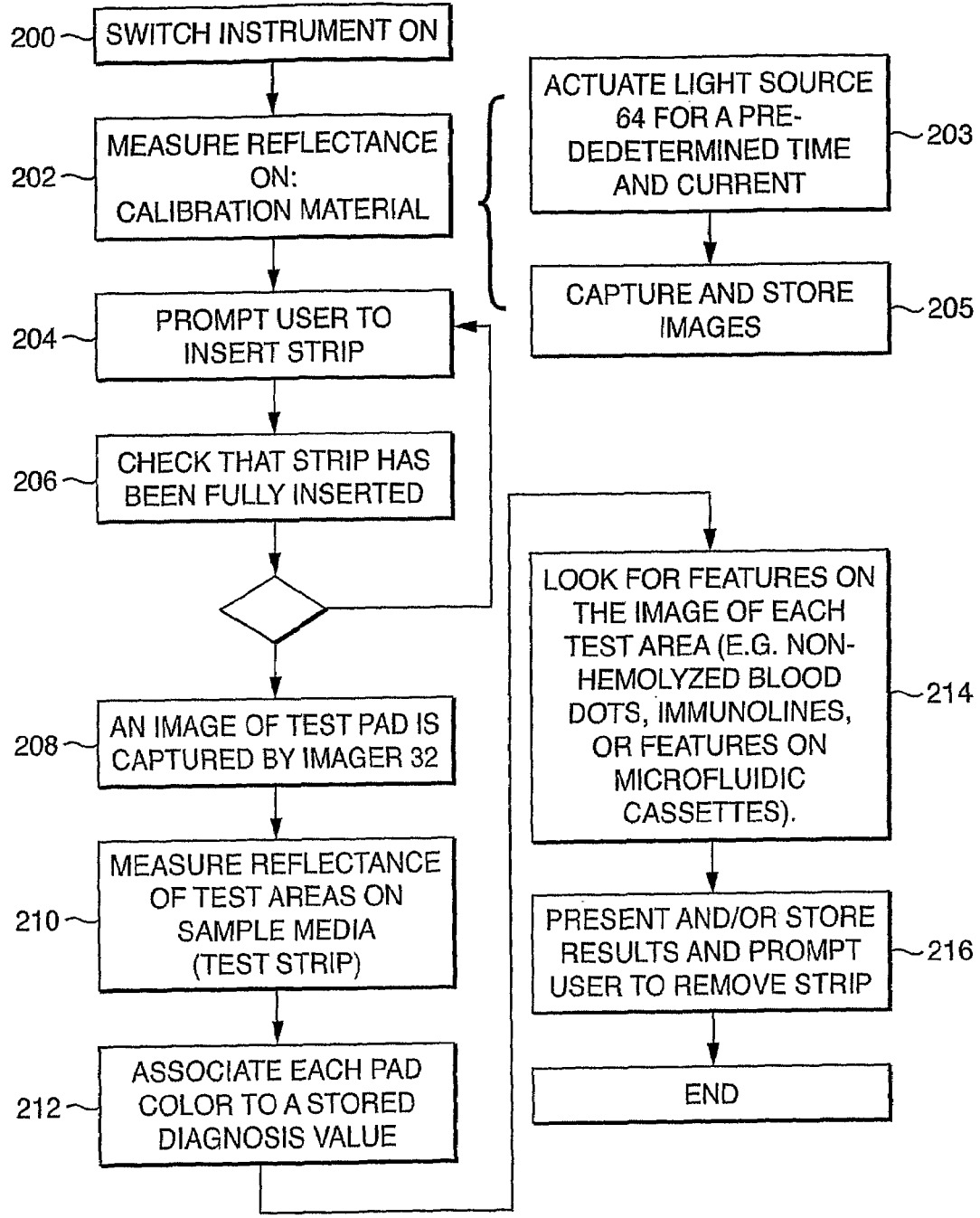
FIG. 9 is a flow chart of operation of embodiments of the present invention.

Having described exemplary embodiments of the invention, the following is a description of the operation thereof. Referring now to FIG. 9, device 100, 100' is initially powered up at 200, after which, reflectance of calibration material is measured at 202. Calibration 202 involves recording and analyzing the reflectance of calibration material 70 that may be either incorporated into holder 26, 26' as described above, or inserted into the holder. Calibration 202 may be effected automatically, e.g., each time device 100, 100' is powered up 200, or may be initiated by the user, for example, in response to an audible prompt and/or a prompt displayed on display 24, 24".

Calibration 202 includes actuating or otherwise exposing device 100, 100' to light source 64 for a pre-determined time and pre-determined current (e.g., when using an electrically actuated source 64) at 203, and capturing and storing images of the calibration material at 205. These calibration images are used to effect sample measurement 210 as discussed in detail below with respect to FIG. 10.

Once calibration is complete, device 100, 100' may prompt the user to insert a test sample 28 at step 204. Upon insertion, at 206, the system checks for an appropriate signal from sensor 66 indicating that sample 28 has been fully inserted. If this signal has not been received, then the system loops back to step 204 to re-prompt the user to fully insert the sample. If the signal was received, then the array 30 of imagers 32 are actuated (e.g., sequentially or simultaneously) at 208 to capture images of each test pad 52. The reflectance of these captured images is then measured 210, with reference to the previously stored values for calibration material 70, which provides a relatively accurate determination of the color of each pad. This test pad measurement 210 is discussed in greater detail below with respect to FIG. 10.

At 212, these reflectance values (colors) are compared to known diagnosis values stored in memory 62, as discussed above. At step 214, the captured images are examined to identify any additional features such as non-hemolyzed blood dots 53 (FIGS. 3 & 4) or immunolines such as test lines on immunoassays, and then compared with known diagnosis values. For example, the presence of particular test lines may be correlated to a diagnosis value of 'pregnancy'. At 216, results (i.e., diagnosis values) generated by steps 212 and/or 214 are then outputted to display 24, 24' and/or stored to memory 62.

Figure 10:
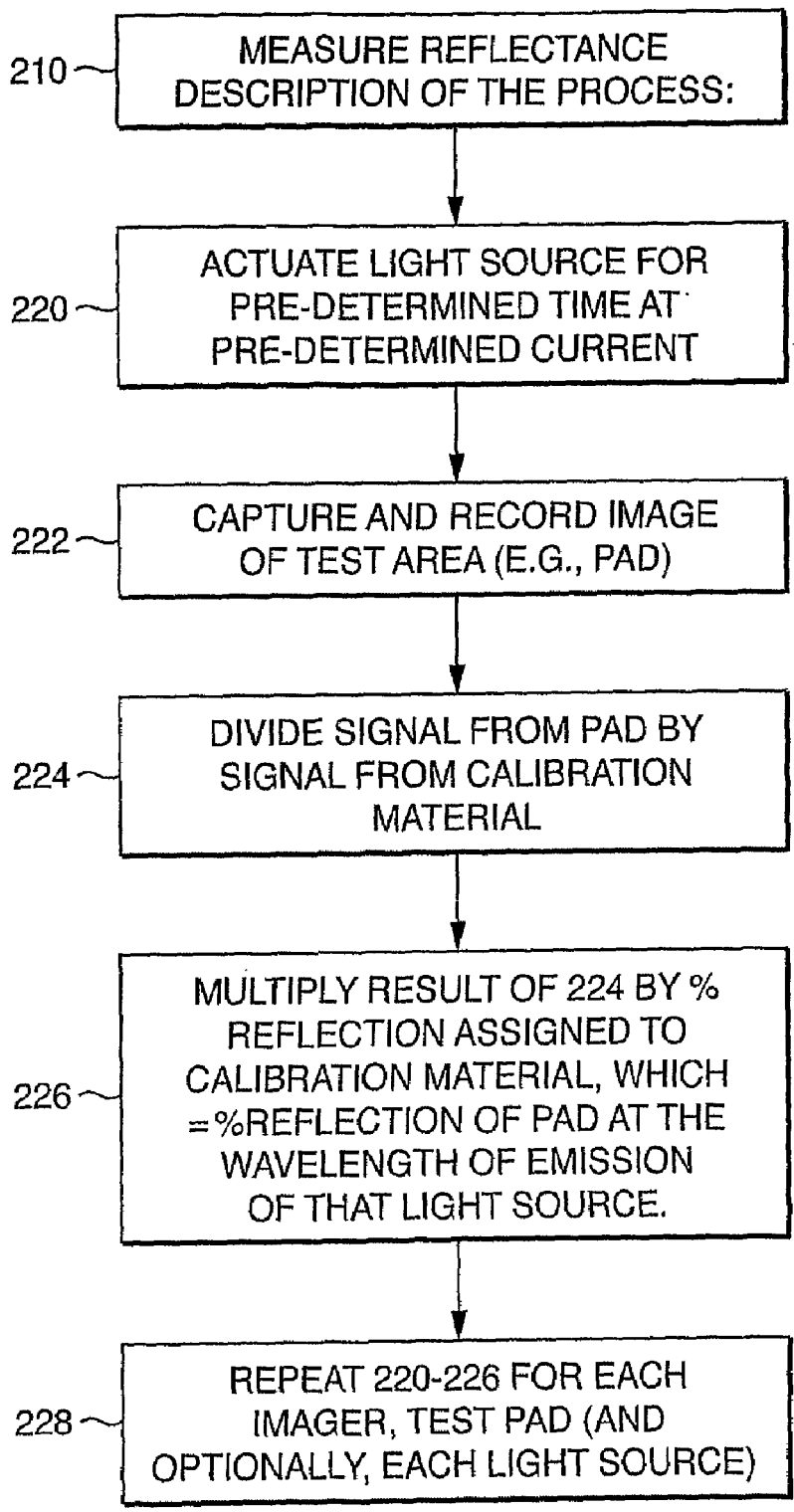
FIG. 10 is a flow chart of measurement steps effected during the operation of FIG. 9.

Turning now to FIG. 10, measurement 210 is discussed in greater detail. As shown, this measurement includes actuating or otherwise exposing device 100, 100' to light source 64 for a pre-determined time and pre-determined current (e.g., for electrically actuated sources) at 220. This pre-determined time and current is preferably the same as that used during steps 203 and 205 of the calibration discussed above. Signals received (i.e., images captured) by imagers 32 are saved to memory 62 at 222. At 224, a numerical value of the reflectance of the image captured at 222 is divided by a numerical equivalent of the reflectance value of the calibration material acquired at step 205 above. At 226, the result of 224 is multiplied by the known percent reflection of the calibration material to generate the percent reflection of the particular pad of sample 28 at the known wavelength of emission of the particular light source 64. This percent reflection corresponds to a color, which may be correlated to known diagnosis values as discussed above. As shown at 228, steps 220-226 may be repeated for each imager and test pad, and optionally, for each light source, in the event light sources of distinct wavelengths (e.g., colors) are used.

Thus, to summarize, the handheld device 100, 100' provides accurate measurement results, eliminates the inflexibility associated with prior reagent test strip readers, and reduces the potential for human error degrading test results. Moreover, these devices provide improved efficiency and compactness relative to prior devices by providing a series of imagers each having relatively small viewing fields that are closely tailored in size to that of the individual test pads 52 being viewed. This construction eliminates the need for any hardware or software that searches for multiple test pads within a single relatively large viewing field. In addition, this construction, including the sliding fit provided by holder 26, 26', obviates any need for complex automated feeders that physically move test strips into desired locations within such large viewing fields. In combination, these aspects advantageously enable the provision of a pocket-size device 100, 100' that may be conveniently carried by a care provider for use during routine patient examination.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

Having thus described the invention, what is claimed is:

1. A self-contained, optical hand-held diagnostic device, the device comprising:
   a body having a pocket-sized form factor sized and shaped for engagement by a user's hand;
   a power supply disposed within said body;
   a display disposed integrally with said body;
   a holder configured for receiving reagent sample media therein, the sample media having a plurality of test areas disposed in spaced relation thereon, each of the test areas configured to react with a sample when disposed in contact with the sample and to change color according to an amount of a constituent or property in the sample;
   the holder sized and shaped for forming an indexed fit with the sample media;
   a micro-array of imagers disposed within said body;
   each of said imagers being superposed with a respective one of the test areas when the sample media is indexed within said holder;
   the imagers being configured to each capture an image of the test area respectively superposed therewith;
   a processor coupled to said imagers;
   said processor configured to analyze said images of said test areas;
   said processor configured to derive a diagnosis value from said analysis, and to generate an output corresponding thereto; and
   said display configured to receive and display said output;
   wherein said device is a unitary, self-contained, pocket-sized diagnostic tool.

2. The device of claim 1, wherein said diagnosis value comprises the amount of said constituent or property.

3. The device of claim 1, wherein said diagnosis value comprises a diagnosis of a condition.

4. The device of claim 1, wherein said sample media includes a test strip, and said test areas include test pads.

5. The device of claim 4, wherein said imagers collectively capture images of the entire test strip.

6. The device of claim 4, wherein each of the imagers is configured to capture an image of a discrete one of the test pads.

7. The device of claim 4, wherein the ratio of imagers to test pads is at least 0.5:1.

8. The device of claim 7, wherein the ratio of imagers to test pads is at least 1:1.

9. The device of claim 1, wherein said array of imagers comprises an array of image capture devices.

10. The device of claim 9, wherein said image capture devices comprise CCD devices.

11. The device of claim 9, wherein said image capture devices comprise CMOS devices.

12. The device of claim 9, wherein said array of imagers comprises a lens subsystem optically coupled thereto.

13. The device of claim 12, wherein said lens subsystem comprises an array of lenses.

14. The device of claim 13, wherein said array of lenses comprises a micro-lens array.

15. The device of claim 12, wherein said lens subsystem is configured to focus the images of the test pads onto respective ones of the image capture devices.

16. The device of claim 1, further comprising a light source configured to illuminate said sample media.

17. The device of claim 1, further comprising a memory device configured for storing diagnostic data.

18. The device of claim 17, comprising a memory device configured for storing calibration data.

19. The device of claim 17, comprising a memory device configured for storing the captured images.

20. The device of claim 1, further comprising a port configured for uploading and downloading data.

21. The device of claim 1, wherein said holder is hingedly coupled to said body.

22. The device of claim 1, wherein said sample media comprises a reagent cassette.

23. The device of claim 1, wherein said sample media comprises a microfluidic device.

24. The device of claim 1, comprising a sensor configured to detect when the sample media is indexed within said holder.

25. The device of claim 24, wherein said sensor comprises at least one of said imagers.

26. The device of claim 25, wherein said at least one imager is configured to detect when the sample media is indexed within said holder by capturing a desired image.

27. A self-contained, optical hand-held diagnostic device, the device comprising:
   a body having a pocket-sized form factor sized and shaped for engagement by a user's hand;
   a power supply disposed within said body;
   a display disposed integrally with said body;

a channel configured for receiving reagent test strip therein, the test strip having a plurality of test pads disposed in spaced relation thereon, each of the test pads configured to react with a sample when disposed in contact with the sample and to change color according to an amount of a constituent or property in the sample;

the channel sized and shaped for forming an indexed fit with the test strip;

a micro-array of imagers disposed within said body in fixed superposition with said channel;

each of said imagers being superposed with a respective one of the test pads when the test strip is indexed within said channel;

a light source configured to illuminate said test strip;

the imagers being configured to each capture an image of the test pad respectively superposed therewith;

a processor coupled to said imagers;

said processor configured to analyze said images of said test areas;

said processor configured to derive the amount of said constituent or property in the sample from said analysis, and to generate an output signal corresponding thereto; and said display configured to receive said output signal and display said amount;

wherein said device is a unitary, self-contained, pocket-sized diagnostic tool.

28. A method for reading reagent sample media, the sample media having a plurality of test areas disposed in spaced relation thereon, each of the test areas configured to react with a sample when disposed in contact with the sample and to change color according to an amount of a constituent or property in the sample, the method comprising the steps of:

(a) receiving the sample media into a holder of a unitary, self-contained, optical hand-held diagnostic device having an integral power supply and display, the holder sized and shaped for forming an indexed fit with the sample media;

(b) with a micro-array of imagers disposed within said body, in which each imager is disposed in fixed superposition with a respective one of the indexed test areas, capturing images of said test areas;

(c) with an integral processor, analyzing said images of said test areas;

(d) deriving said amount of said constituent or property in said sample from said analysis;

(e) generating an output signal corresponding to said amount; and (f) transmitting said output signal to the integral display.

29. The method of claim 28, wherein said sample media includes a test strip, and said test areas include test pads.

30. The method of claim 28, further comprising the step of calibrating the device.

31. The method of claim 30, wherein said calibrating comprises capturing an image of a calibration material of known reflectance.

32. The method of claim 31, wherein said deriving comprises:

dividing the reflectance of said image of said test pad by the reflectance of said image of a calibration material; and multiplying the result of said dividing by the known reflectance of the calibration material to generate a calibrated percent reflectance of the test pad.

33. The method of claim 32, wherein said deriving further comprises comparing the calibrated percent reflectance with known values of amounts of said constituent or property at various predetermined percent reflectances, to determine the amount of said constituent or property at said calibrated percent reflectance.

34. The method of claim 32, comprising comparing the calibrated percent reflectance with known values stored within a look-up table.

35. The method of claim 33, wherein said deriving further comprises comparing said amount of said constituent or property to known diagnoses associated with various predetermined amounts of said constituent or property, to determine a diagnosis that corresponds to said amount of said constituent or property.

36. The method of claim 35, wherein said generating comprises generating a signal corresponding to said amount of constituent or property and to said diagnosis.

37. The method of claim 36 further comprising the step of displaying said amount of constituent or property and said diagnosis on said integral display.

38. The method of claim 28 further comprising the step of illuminating said test areas.

* * * * *